United States Patent [19]

Larsson

[11] Patent Number: 5,723,601
[45] Date of Patent: Mar. 3, 1998

[54] SUPER POROUS POLYSACCHARIDE GELS

[75] Inventor: Per Olof Larsson, Lund, Sweden

[73] Assignee: Pharmacia Biotech AB, Upsala, Sweden

[21] Appl. No.: 302,839

[22] PCT Filed: Mar. 16, 1993

[86] PCT No.: PCT/SE93/00226

§ 371 Date: Sep. 16, 1994

§ 102(e) Date: Sep. 16, 1994

[87] PCT Pub. No.: WO93/19115

PCT Pub. Date: Sep. 30, 1993

[30] Foreign Application Priority Data

Mar. 18, 1992 [SE] Sweden ................................ 9200827

[51] Int. Cl.$^6$ ............................................ C08B 37/16
[52] U.S. Cl. ................ 536/165; 536/112; 536/114; 536/123.1; 536/124; 55/67; 73/19.2
[58] Field of Search ................... 536/20, 46, 55.1, 536/103, 114, 112, 123.1, 124; 55/67; 73/19.2

[56] References Cited

U.S. PATENT DOCUMENTS 4,741,872  5/1988  De Luca et al. ........................ 264/4.7
4,935,365  6/1990  Nilsson et al. .
5,019,270  5/1991  Afeyan et al. .

FOREIGN PATENT DOCUMENTS

A2 0222718  5/1987  European Pat. Off. .
WO A1
8911493  11/1989  WIPO .
WO A1
9100762  1/1991  WIPO .

*Primary Examiner*—Duc Truong
*Attorney, Agent, or Firm*—Birch, Stewart, Kolasch & Birch, LLP

[57] ABSTRACT

Porous material of a polysaccharide and a method for preparations of such a material, wherein a water-based solution of the polysaccharide is mixed, with controlled stirring, with an essentially water-immiscible organic phase to form an emulsion, which when allowed to solidify, just before or during the gelling process, forms a network of two continuous phases, an aqueous polysaccharide phase and a flow-pore-forming organic phase, resulting in a material with two types of pores: small diameter diffusion pores and large diameter flow through pores.

31 Claims, No Drawings

SUPER POROUS POLYSACCHARIDE GELS

This application is a 371 of PCT/8E/93/00226 filed Mar. 16, 1993.

The present invention is related to polysaccharide gels containing, besides pores of a molecular dimension, for instance 20–500 Å, also interconnected macroscopic pores, typically with a pore diameter about 0.5–500 micrometers. These new materials have been found to considerably broaden the application areas for polysaccharide gels which have many advantageous characteristics for use in biotechniques, like chromatographic separations, membrane separation technology and support for solid phase chemistry, especially in biologically sensitive systems.

These superporous polysaccharide gels are produced by mixing a water-containing solution of the polysaccharide with an essentially water immiscible organic phase under vigorous stirring whereafter the finely dispersed mixture is allowed to solidify and the organic phase finally is washed away. The above organic phase is the superpore-forming phase. It must therefore be composed in such a way that it can exist as a continuous phase in the presence of a continuous agarose phase.

The new polysaccharide gels may be produced in various shapes, for instance more or less regular beads like spheres, membranes, etc. and can be used as a base matrix for the manufacture of chromatographic media, and as a carrier matrix in general for various biomolecules like cells, enzymes, antibodies etc.

Polysaccharide gels are known to play an important role for the manufacture of materials for separation of mixtures of biomolecules. Among the characteristics making these gels especially interesting can be mentioned their inertness in contact with proteins and other biomolecules and their porous structure. A further important property is their resistance against alkaline conditions, which is of great importance in large scale separation processes requiring frequent regeneration/sterilization of the gel. Polysaccharide gels unlike many other separation materials allow such in situ regeneration with, for instance 1M NaOH, which is an effective agent, frequently used for purification and sterilization.

Polysaccharide gels are used for various types of chromatography. One such example is gel filtration, whereby the sample constituents are size fractionated. This is an application where the inertness is of crucial importance since any interaction between the gel material as such and the sample molecules makes the separation less effective and might even completely destroy the result. Commercially very important materials for this type of separation have, for many years, been produced from crosslinked dextran and native or optionally crosslinked agarose (for instance Sephadex and Sepharose from Pharmacia LKB Biotechnology AB, Uppsala, Sweden).

Another example of a commercially important chromatographic technique is ion exchange chromatography. Several materials for ion exchange chromatography are derived from dextran, agarose or cellulose. The choice of polysaccharide gels as the carrier matrix is based, as above, on their inertness and a well established derivatization chemistry for the introduction of ion exchange groups.

A further example is affinity chromatography. Again, polysaccharide gels are preferred in many applications due to the number of convenient techniques available for introducing the affinity ligands and the minimum of unspecific binding of biomolecules.

The polysaccharide gels accordingly have several important characteristics making them an obvious choice as a base matrix for the preparation of materials for chromatographic separation. The gels exhibit, however, also certain drawbacks, like the limited mechanical stability. This is not a real problem when comparatively large gel beads (around 0.1 mm) are used as in traditional chromatography with the low flow rates through the gel bed required for diffusion reasons. The situation is, however, quite different when attempts are made to increase the separation efficacy by the use of smaller gel beads (around 5–20 micrometers). At flow rates optimal for diffusion reasons, the pressure drop in the gel bed is so high that the polysaccharide beads will collapse. It has been possible to extend the use of, for instance, agarose in systems with increased flow rates by crosslinking, but in pronounced high pressure systems only particles of mechanical stability similar to silica and polystyrene have been used. Most materials in this group are, however, considerably less compatible with proteins, they are not so easy to derivatize as polysaccharides and they can not be regenerated at high pH-values.

I have now found that high performance polysaccharide gels can be produced by introducing macropores which are interconnected to give flow passages, channels, through the gel. Besides these so called super pores which are in the range of from 0.5–1000 micrometers, like 0.5–500, and preferably 5–100 micrometers, pores about 30–500 Å, typical for polysaccharides, are also present. The materials accordingly have two distinct groups of pores distinguishing them from polysaccharide materials known from the prior art. When these new materials are packed in a chromatographic column and a liquid flow is applied through the column some of the flow will pass through the particles via the superpores. The substances to be separated are thus transported also to the inner parts of the beads by convective flow, which is a much faster way of transportation than diffusion, which is the only way of transport in prior art materials.

Only short distances have to be covered by diffusion in the new materials and the particles will therefore, in spite of a much larger particle size, be as effective as a prior art particle, and still giving rise to a much lower pressure drop over the gel bed. The invention accordingly discloses a solution to the problem of how to make polysaccharide gels, useful also in High Performance Liquid Chromatography (HPLC). Another advantage exhibited by the new materials is their use in the separation of cells, chromosomes and other macromolecules which are too large to have access to the pores normally found in polysaccharide gels. A further advantage is that the new materials can be used in electrophoresis, including capillary electrophoresis, and as a carrier for catalytically active cells and enzymes. The flow in macropores, which has been found to be advantageous in chromatographic separation, enhances the mass transport of substrates and products, thereby improving the catalytic efficiency.

The technique of utilizing throughpores in chromatographic separation is described by Afeyan el al in U.S. Pat. No. 5,019,270. They mention the use of certain polymers, especially styrene and acrylate based materials, but there is no teaching how to prepare polysaccharide gels useful in the claimed method.

It is known that polysaccharides can be produced to contain macropores, see for instance U.S. Pat. No. 4,935,365 (Mosbach et al). A gel, as described in U.S. Pat. No. 4,935,365, will have a considerably larger surface area due to the macropores, a fact which increases its use in some applications, like cell culture and also in certain chromatographic techniques. The macropores are, however, not interconnected and there is accordingly no through flow via these pores which clearly distinguish the prior art gels from the present materials.

The invention is accordingly related to polysaccharide gels characterized by having, besides pores of molecular dimension, like 20 to 500 Å, also interconnected, continuous macropores with a pore diameter, preferably in the range of from 5 to 100 micrometers, as well as the preparation of such gels at various shapes.

A broad group of polysaccharides can be used as the base substance for the preparation of materials according to the present invention and among these can be mentioned agar, agarose, alginate, dextran, carrageenan, chitosan, cellulose and starch, as well as mixtures of these. The actual choice will normally be determined by the desired properties of the final product, for instance with regard to pore size, charge, stability in various media, cost, etc.

The amount of superpores in a material according to the invention may vary considerably, but a range of from around 15-50% will cover most applications. The basic requirement that also the polysaccharide phase must be continuous has indicated that the range of from 25-40% is preferred. The use of this interval has also been found to facilitate that a desired diameter, as well as a desired distance between the super pores, is achieved.

The superpore diameter can, as mentioned above, be varied within a wide range, and are greater than 0.5 micrometer, preferably greater than 5 micrometer, and smaller than 1 mm, preferably smaller than 0.5, especially smaller than 0.1 mm. This gives a prefered interval around 5-100 micrometers, but in certain applications values outside this range are useful and even desired, for instance 0.5 to 1000 micrometers. The choice of pore diameter depends primarily on the intended application and the physical shape of the material to be produced. When the gel is produced as discrete particles to be packed in beds, for instance in a column, the diameter of the macropores should be proportional to the particle diameter for an optimal flow through the interconnected pores. The relationship can be estimated according to the following model: The super pores are approximated as tubes and so are also the interstitial spaces between the beads. In a normal bed of packed monodisperse spheres the diameter of such interstitial pores is approximated to be ¼ of the particle diameter. In order to function with the best efficiency, the linear flow through the super pores in a chromatographic bed of superporous particles should be the same as the flow in the interstitial pores. This is achieved when the diameter of the super pores is about the same as the diameter of the interstitial pores. However, taking into account a certain particle size distribution that will diminish the interstitial pore size, the ideal size of a superpore should be around ⅙ of the particle diameter. Smaller superpores give a less satisfactory pore flow but are still very much improving the chromatographic properties of the bed. Thus, the size of the super pores should preferably be in the range of from ⅙ to 1/10 of the particle diameter.

Simple geometric calculations show that the average thickness of the polysaccharide phase will be approximately the same as the superpore diameter when the particle has the preferred content of super pores, i.e. about 33% (v/v). A bed packed with optimally designed super porous particles with a diameter d could therefore be expected to have a chromatographic efficiency approaching that of a bed packed with prior art particles with a diameter d/6, at least in diffusion controlled situations. Most significantly, the pressure drop with the super porous particles would be only about 1/36 of the pressure drop with the prior art particles (the pressure drop is inversely proportional to the square of the particle diameter).

When the new materials are prepared as a continuous bed instead of discrete particles it is evident that all flow must pass through the super pores giving somewhat different aspects to be considered when designing the system. When the superpore diameter is made small, the closer such pores will be situated, with the advantage that only small distances have to be covered by diffusion. However, the back pressure will increase when the pores are made smaller (the back pressure is inversely proportional to the square of the superpore diameter). This means in practice that in a deep bed the superpore diameter should not be less than about 20 micrometers if the material has a volume fraction of super pores around ⅓, to still give an acceptable flow through the bed.

In a thin membrane (0.1 to 3 mm) a very small superpore diameter can still be utilized, and values even less than 20 micrometers are accessible. On the other hand, by making the superpores larger, it is possible to produce membranes with very small back pressure.

The fraction of polysaccharide phase in a continuous bed as mentioned above can be up to at least 80%, while the corresponding values for a normal packed prior art bed and a packed superporous bed are 60-70% and 40%, respectively.

When producing a polysaccharide gel according to the invention a water-based polysaccharide phase is mixed, with vigorous stirring, with an essentially water-immiscible organic phase, consisting of one or more components, usually an organic solvent and a detergent of the type stabilizing "oil in water" systems. The emulsion so formed, Emulsion 1, must have certain characteristics for a product according to the present invention to be formed, and this will discussed at some length further below.

The emulsion is subjected to various treatment depending on the geometrical shape of the material that is to be produced:

(a) Preparation of Superporous Spherical Particles

Emulsion 1 is mixed with stirring with an essentially water immiscible organic phase comprising one or more components, usually an organic solvent and a detergent of the type stabilizing "water in oil". Drops of Emulsion 1 are formed. The drop size depends on the stirring speed and the concentration of detergent 2. The polysaccharide phase in the drops is allowed to solidify, for instance by lowering the temperature below the gelling temperature of the polysaccharide.

In an alternative embodiment small drops of Emulsion 1 are formed by a nozzle. The drops leaving the nozzle in a stream will solidify when they pass through the atmosphere or when they are collected in a bath containing complexing agents. Solid particles formed according to any of the methods presented above are collected and washed for instance with water, water-ethanol, water-acetone or some other water-miscible solvent.

(b) Superporous Fibres

Emulsion 1 is pumped through one or more nozzles into a bath, with a temperature below the gelling temperature of the polysaccharide, or containing complexing agents. The fibres so formed are retained and washed as above (a).

(c) Superporous Continuous Beds

The beds are moulded in suitable containers, for instance columns for chromatography. Emulsion 1 is poured into the container and the polysaccharide phase is brought to solidify by lowering the temperature of the column to a value below the gelling temperature of the polysaccharide. The organic phase in the superporous gel bed is removed by pumping water and a water miscible solvent through the bed.

(d) Superporous Membranes

Emulsion 1 is moulded as a thin layer in an equipment consisting of two parallel glass plates which are sealed together at the ends. The polysaccharide phase is brought to solidify, for instance by lowering the temperature, and the organic phase is removed by washing the gel sheet with water and a water-miscible solvent.

(e) Irregular Superporous Particles

Superporous fibres (b) or superporous gel beds (c) are ground to a suitable particle size and then fractionated, for instance by wet-sieving.

The Emulsion 1 should as mentioned above fulfil certain criteria and such characteristics of importance are the type of polysaccharide phase, the concentration of polysaccharide in the phase, volume fraction of organic phase, the composition of the organic phase, the micro structure of the organic phase, the stirring intensity during the formation of Emulsion 1 and the relationship between the time during which it is formed and subsequent solidified. This is a series of interrelated parameters defining a rather complex reaction scheme. Two quick tests are available for verifying that a given combination will give a system suitable for the preparation of the actual materials. The first test involves study of Emulsion 1 under a microscope. The crucial factor is that the two phases must readily form a network of two continuous phases.

When studying emulsion systems solidifying over room temperature, for instance agarose, the use of a thermostatted object glass will considerably facilitate the inspection, since otherwise gellation might occur to early. The use of organic phases tinted with a water immiscible dye, for instance Sudan Yellow, could also be of certain help.

The second, complementary, test involves a function test of pore flow. A small sample of Emulsion 1 is solidified an a thin (about 1 mm thickness) gel slice is prepared. The gel slice is placed on a supporting net and a water jet is directed towards the gel surface. If suitable super pores are present the water jet will readily displace the organic phase in the gel slice. The appearance of the gel slice will change from white to semi-transparent in this process.

Of special importance for the characteristics of Emulsion 1 is the composition of the organic phase and the stirring intensity during formation of the emulsion. The organic phase comprises in most cases a mixture of an organic solvent and a detergent. The essentially water-immiscible solvent can for instance be selected from the group comprising cyclohexane, heptane and toluene. The detergent, which should be of the type stabilizing "oil in water" emulsions and is preferably of the type represented by Tween 80 (polyoxyethylene sorbitan mono-oleate) or Tween 20 (polyoxyethylene sorbitan mono-laurate).

The, at present, preferred method of preparing Emulsion 1 involves an organic solvent and comprises the following steps: The detergent is finely dispersed in the organic solvent, for instance by vigorous stirring to form the organic phase, which is thereafter mixed with the water-based polysaccharide phase under controlled stirring. If Emulsion 1, when inspected under a microscope as described above, readily separates into two continuous phases in a mosaic pattern, it is clearly indicated to have the correct properties for the preparation of superporous gels. Further inspection of the continuous pore forming organic phase reveals important information. The phase is not homogeneous but comprises discrete, microscopic drops of solvent in a continuous detergent phase. The solvent drops may be characterized as bulking material in a continuous detergent phase. If Emulsion 1, on the other hand, is not suitable for production of superporous materials drops of the organic phase appear isolated in the polysaccharide phase and show no tendency to aggregate to a continuous organic phase.

Of particular importance for the design of materials with continuous, interconnected superpores is the observation that Emulsion 1, prepared in the preferred way comprises a continuous polysaccharide phase and a continuous organic phase, which in turn is composed of a continuous detergent phase and suspended droplets of an organic solvent. Some guidance for the preferred design of emulsion 1 can be given: The observation that Emulsion 1, when useful according to this invention, comprises a continuous detergent phase with drops of solvent, is of essential importance for the design of materials with interconnected superpores. Some guidances can be given:

(a) Since the detergent, and not the solvent, forms the continuous part of the superpore forming organic phase, it is important that there is enough of the detergent. If the amount of detergent is too low, all of it will be "consumed" for stabilizing the boundary surfaces between the solvent drops and the water-based polysaccharide. The lack of "free" detergent molecules prevents the formation of continuous superpores.

(b) The stirring velocity, or, in other words, the energy created by a stirrer, is important for the formation of superpores. An increased stirring velocity results in smaller solvent drops with the consequence that more detergent is required for stabilizing the boundary surface against the water-based polysaccharide phase. This means that a certain composition of Emulsion 1, produced at a low stirring speed of for instance, 500 rpm, may give a superporous product, whereas a higher speed, for instance 2000 rpm, may not give a super porous product.

(c) The volume fraction of super pores is mainly a function of the amount of organic phase in Emulsion 1.

(d) The diameter of the super pores as well as the amount of super pores in the material, is primarily determined by the detergent concentration, the stirring speed and the time interval between the formation of Emulsion 1 and the solidifying of the polysaccharide.

Keeping all the other parameters constant, it has been found that (1) an increased detergent concentration (expressed in % of the total organic phase) will result in a larger superpore diameter, but a smaller number of such pores in the material.

(2) an increased stirring speed will result in a higher number of superpores with a smaller diameter.

(3) a longer time interval between the formation of Emulsion 1 and the solidifying of the polysaccharide phase to give a smaller amount of super pores, which however have a larger diameter.

From the above discussion, and also the following Examples, it is apparent that the stirring time and the stirring rate at various steps of the manufacturing process can be controlled and modified to produce the desired product.

From the guide-lines given above it is evident that the continuous organic phase in Emulsion 1 comprises essentially a detergent with microscopic solvent drops as bulk substance. This indicates that it would be possible to produce a functioning Emulsion 1, even without an organic solvent. This has also been found to be the case and superporous membranes have been produced from a mixture of a warm agarose solution and the detergent Tween 80 which was cooled enough to solidify. The rules given above are of course somewhat modified in this embodiment of the invention, since there are no solvent drops to be stabilized.

Porous materials according to the invention, when produced in spherical form for use in chromatographic separations, have a ratio between the flow pore diameter and the particle diameter within the range of from 0.01–0.3, preferably 0.05–0.2.

The invention will now be illustrated by a series of examples how to prepare a polysaccharide gel according to the invention as well as its use in chromatography.

EXAMPLE 1

Preparation of Emulsion 1 Based on Agarose
(Preferred Embodiment)

Solution A 6.0 g agarose powder was suspended in 94 ml of water, which was heated to 92° C. and kept at that temperature for 1 minute for dissolving the agarose. The agarose solution was then cooled to 60° C.

Solution B 3.0 ml of the detergent polyoxyethylene sorbitan monooleate (Tween 80) was suspended in cyclohexane and the volume of the mixture was adjusted to 50 ml and heated to 60° C. with stirring. Immediately before further use it was stirred vigorously.

Solution B was then mixed with Solution A in a thermostatted (60° C.) container, equipped with a stirrer, which was kept at 1200 rpm for two minutes. A white viscous emulsion was formed (Emulsion 1).

EXAMPLE 2

Preparation of Emulsion 1 Based on Agarose
(Alternative Embodiments)

Solutions A and B were prepared analogous to Example 1, see Table 1 for details regarding compositions and results. Whether a certain mixture was suitable for producing superporous materials or not was determined by the following test: A 5–10 ml sample of Emulsion 1 was allowed to solidify in a test tube by lowering the temperature. The gel so formed was cut in thin slices which were washed with water or 50% ethanol. The slices were then studied by a microscope and the presence or absence of interconnected superpores was easily established.

TABLE 1

A is the amount of agarose in %. For B is indicated the organic solvent chosen and the amount of detergent, Tween 80, in %.

| Exp | A | B | B | A/B (W/W/) | Speed (rmp) | Super-pores | Pore diam. |
|---|---|---|---|---|---|---|---|
| 1 | 6 | c.h. | 1 | 2 | 2000 | No | — |
| 2 | 6 | c.h. | 1 | 2 | 500 | No | — |
| 3 | 6 | c.h. | 3 | 2 | 2000 | Yes | 25 |
| 4 | 6 | c.h. | 3 | 2 | 500 | Yes | 40 |
| 5 | 6 | c.h. | 10 | 2 | 2000 | Yes | 100 |
| 6 | 6 | c.h. | 10 | 2 | 500 | Yes | 125 |
| 7 | 6 | c.h. | 40 | 2 | 2000 | No | — |
| 8 | 6 | c.h. | 40 | 2 | 500 | No | — |
| 9 | 6 | — | 100 | 2 | 2000 | Yes | — |
| 10 | 6 | — | 100 | 2 | 500 | Yes | — |
| 11 | 6 | c.h. | 1 | 1 | 2000 | No | — |
| 12 | 6 | c.h. | 1 | 1 | 500 | Yes | — |
| 13 | 6 | c.h. | 3 | 1 | 2000 | Yes | 20 |
| 14 | 6 | c.h. | 3 | 1 | 500 | Yes | 40 |

TABLE 1-continued

A is the amount of agarose in %. For B is indicated the organic solvent chosen and the amount of detergent, Tween 80, in %.

| Exp | A | B | B | A/B (W/W/) | Speed (rmp) | Super-pores | Pore diam. |
|---|---|---|---|---|---|---|---|
| 15 | 6 | c.h. | 15 | 1 | 2000 | No | — |
| 16 | 6 | c.h. | 15 | 1 | 500 | No | — |
| 17 | 6 | h. | 1 | 1,5 | 2000 | No | — |
| 18 | 6 | h. | 1 | 1,5 | 500 | Yes | — |
| 19 | 6 | h. | 5 | 1,5 | 2000 | Yes | 10 |
| 20 | 6 | h. | 5 | 1,5 | 500 | Yes | 15 |
| 21 | 6 | h. | 20 | 1,5 | 2000 | No | — |
| 22 | 6 | h. | 20 | 1,5 | 500 | No | — |
| 23 | 6 | s.o. | 1 | 1,5 | 2000 | No | — |
| 24 | 6 | s.o. | 1 | 1,5 | 500 | Yes | 10 |
| 25 | 6 | s.o. | 5 | 1,5 | 2000 | Yes | 30 |
| 26 | 6 | s.o. | 5 | 1,5 | 500 | Yes | 50 |
| 27 | 6 | c.h. | 5* | 2 | 1200 | Yes | 40 |
| 27 | 8 | c.h. | 4 | 2 | 1200 | Yes | — |
| 28 | 5 | c.h. | 4 | 2 | 1200 | Yes | — | c.h. = cyclohexane; h. = heptane
Tw.20 = Tween20 (polyoxyethylensorbitanmonolaurate)
s.o. = Soybean oil

EXAMPLE 3

Preparation of Superporous Spheres—Standard Method 100 ml of Emulsion 1 prepared according to Example 1 was, with a stirring of 600 rpm, poured into 200 ml cyclohexane (thermostatted to 60° C.), containing 4% (v/v) Span 85 (Sorbitan trioleate). After 0.5 minutes the mixture was cooled to 20° C., and spherical, superporous particles were formed.

The particles were filtered off, washed with water, 50% ethanol and finally water.

In an alternative experiment the agarose solution was stirred at 600 rpm at 60° C., and the organic phase (comprising cyclohexane and Span 85) was added. After 0.5 minutes the mixture was cooled to room temperature. The superporous particles were treated as above.

The experiment was repeated by using an emulsion prepared according to Example 2, at various stirring speed, resulting in superporous particles covering a range of pore diameters and particle diameters.

A product with a desired size distribution could in each case easily be obtained by wet sieving.

EXAMPLE 4

Preparation of Superporous Membranes

The membranes were moulded in a container formed by two glass plates (20×20 cm), kept in parallel at a distance of 0.5 to 5 mm. Emulsion 1 from Example 1 or Example 2 was poured into the container which was thermostatted to 60° C. After 0.5 minutes the container was cooled to room temperature and the emulsion was allowed to solidify. The superporous membrane sheet so formed was released and washed with water, 50% ethanol and water. Round membranes were punched from the sheet and used in conventional membrane filter holders.

EXAMPLE 5

Preparation of a Continuous, Superporous Agarose Bed

An emulsion according to Example 1 was poured into a thermostatted (60° C.) column for chromatography (a glass tube with a diameter of 1.6 and a height of 20 cm), sealed in one end with a silicone plug. The tube was cooled to room temperature and an agarose gel was formed. The cylindrically formed gel plug was pressed out of the tube and the two end surfaces were cut perpendicular to the a cylinder axis. The gel plug was then inserted into the chromatographic tube which was connected to a peristaltic pump of the type used in chromatography. The organic phase containing the detergent was removed by washing the gel with water, 50% ethanol and finally with another portion of water.

EXAMPLE 6

Crosslinking with Divinylsulfone 10 g superporous particles prepared according to Example 3 were suspended in 10 ml potassium phosphate buffer (pH 12.3) and 100 mg sodiumborohydride was added. After the addition of 0.5 ml divinylsulfone (DVS), crosslinking was allowed to proceed for 4 hours on an oscillating table. The product was then repeatedly washed with water on a glass filter. This treatment increased the mechanical stability of the particles by a factor of about 4.

EXAMPLE 7

Preparation of Superporous Anion Exchanger Particles

Superporous agarose particles prepared according to Example 3 were reacted with DVS analogous to Example 6. After the final washing the particles were immediately suspended in 50 ml 10% polyethyleneimine solution (molecular weight of about 60,000) adjusted to pH 9.5 by HCl. The particles suspension was stirred for 16 hours at room temperature and then washed on a glass filter with water, 0.1M sodium chloride and water.

EXAMPLE 8

Preparation of CNBr-Activated Superporous Agarose Particles 25 g of superporous agarose particles prepared according to Example 3 were suspended in 50 ml iced 1M sodium carbonate, pH 12.1. The suspension was stirred and a CNBr-solution (0.75 g CNBr+1.5 ml acetonitrile) was added. After 1.5 minutes an equal amount of CNBr-solution was added and the activation was terminated after 4 minutes by washing the particles on a glass filter with 0.5 liter ice water, 100 ml 0.2M phosphate buffer (pH 8.5) and finally 0.5 liter ice water. The so activated gel was used for coupling of various ligands.

EXAMPLE 9

Preparation of a CNBr-Activated Continuous Superporous Gel Bed

A cylindrical, continuous, superporous agarose bed with the dimension 1.6×6 cm was prepared analogous to Example 5 and inserted into a column with a flow adaptor. The column was connected to a heat exchanger (a 50 cm×1/16" tube of stainless steel) and a peristaltic pump. The column as well as the heat exchanger were placed in an ice bath and 50 ml iced 1M sodium carbonate was pumped through the column. 50 ml activation solution (2.5 g CNBr dissolved in 1M sodium phosphate buffer, pH 12.1) was pumped through the column for 5 minutes whereafter the activated gel bed was washed with 100 ml iced water, 50 ml iced 0.2M sodium phosphate buffer (pH 8.5) and 50 ml water. The gel was immediately used for coupling of various ligands.

EXAMPLE 10

Preparation of Superporous NAD-Agarose Particles 20 g superporous CNBr-activated particles, prepared according to Example 8, were mixed with 10 ml iced 0.2M phosphate buffer, pH 8.5, and 5 ml iced NAD-analogue solution (10 mg $N^6$-[(6-aminohexyl)kabamoylmethyl)]-NAD). After adjusting the pH to 8.5 the suspension was stirred for 16 hours at room temperature. The superporous particles were filtered off and suspended in 0.2M glycine-NaOH buffer, pH 8.7 for 15 minutes, for removing any remaining active groups. The superporous NAD particles were washed with 0.5 liter water and 0.5 liter 1 mM acetate buffer, pH 5.0. The particles were stored in a cold-storage room.

EXAMPLE 11

Preparation of a Superporous Continuous NAD-Agarose Bed

A CNBr-activated superporous continuous gel bed (1.6×6 cm), prepared according to Example 9 was packed in a column with flow adaptors. A 10 ml iced solution containing 200 mg NAD-analogue (10 mg $N^6$-[(6-aminohexyl) kabamoylmethyl)]-NAD) in 0.1M sodium phosphate buffer, pH 8.5, was circulated through the column. After 1 h the temperature in the circulating system was raised to room temperature. 16 hours later the coupling reaction was terminated and a 0.2M glycine-NaOH buffer, pH 8.7, was pumped through the column for 15 minutes to inactivate any remaining active groups. The superporous continuous NAD-agarose was washed with 100 ml water and 100 ml sodium acetate buffer, pH 5. The gel bed was finally stored in a cold-storage room.

EXAMPLE 12

Preparation of Superporous, Continuous Gel Beds Derivatized with Biomimetic Dyes A superporous gel bed with the dimension 1.0×5 cm was prepared analogous to the method described in Example 5. A solution containing 12.5 ml water, 125 mg dye, 3 ml 20% sodium chloride and 3 ml 2.5M sodium carbonate was recirculated through the bed for 16 hours, whereafter the gel was washed with 100 ml 1M sodium carbonate and 500 ml water.

The following reactive triazine dyes were used: Procion Blue H-Erd, Procion Orange, Procion Green, Procion Yellow, Procion Red and Cibacron Blue 3GA.

EXAMPLE 13

Comparison Between Prior Art and Superporous Particles as Carrier Matrices for Gel Filtration The superporous agarose particles were prepared according to Example 3 and the prior art particles were prepared by dispersing 6% agarose solution in cyclohexane (60%) essentially as described for emulsion 1 in Example 3. Particles of the two types having a diameter of 0.4 mm were packed in chromatography columns (1.6×16.5 cm) which were connected to a HPLC system comprising pump, sample injector, UV detector and plotter. The sample consisted of low molecular substance (sodium azide) and a high molecular substance (bovine serum albumin—BSA). The samples were injected and the elution profiles were recorded for effective theoretical plate height calculations (HETP). The lower HETP values obtained in experiments with superporous particles clearly indicate that these are superior compared to the prior art particles. This is especially true in experiments with high flow rates and high molecular substances, for instance experiments 8 and 9.

TABLE 2

| Exp | | Flow rate | HETP value | |
|---|---|---|---|---|
| No | Substance | cm/min(mm) | normal | superporous |
| 1 | $NaN_3$ | 0.1 | 1.8 | 0.5 |
| 2 | $NaN_3$ | 0.5 | 2.3 | 0.9 |
| 3 | $NaN_3$ | 1.0 | 3.0 | 1.0 |
| 4 | $NaN_3$ | 2.0 | 3.6 | 1.4 |
| 5 | BSA | 0.1 | 3.0 | 2.0 |
| 6 | BSA | 0.15 | 7.3 | 2.2 |
| 7 | BSA | 0.25 | 12 | 2.4 |
| 8 | BSA | 0.5 | 18 | 2.5 |

EXAMPLE 14

Comparison Between Affinity Chromatography Materials Produced From Prior Art and Superporous Particles Superporous NAD-agarose particles prepared according to Example 10 were packed in a chromatography column (1.6×5 cm). The NAD-agarose particles had a diameter of 0.4 mm and a static binding capacity for lactate dehydrogenase of 10 mg/g gel in the presence of 25 mM oxalate. Another column with the same dimensions was packed with prior art agarose particles (Example 13) with the same concentration of NAD-analogs (the substitution was carried out as in Example 10. Both columns had the same particle diameter and the same binding capacity. The columns were compared with respect to their ability to adsorb lactate dehydrogenase from a raw extract, in the presence of 25 mM sodium oxalate. 50 ml of the raw extract was pumped through each of the columns with a speed of 3 or 9.9 ml/min. The outflow from the columns was analyzed with regard to protein concentration and lactate dehydrogenase activity. The columns were then washed and the adsorbed enzyme eluted with 1 mM NADH. The following results were obtained:

| Flow | Adsorbed enzyme (% of applied) | | Eluted enzyme (% of applied) | |
|---|---|---|---|---|
| ml/min | normal | superporous | normal | superporous |
| 3.0 | 90 | 100 | 100 | 90 |
| 9.9 | 50 | 90 | 50 | 90 |

The results clearly shows that when the flow rate is increased from 3.0 to 9.9 ml/min the prior art agarose material becomes considerably less effective while the superporous gel shows approximately the same behaviour. This indicates that the operative capacity of the superporous gel is about three times the corresponding value of a prior art agarose gel.

I claim:

1. A method for producing porous materials of a polysaccharide, comprising the steps of:
   mixing a water-based solution of the polysaccharide, with stirring, with an essentially water-immiscible organic phase to form an emulsion; and
   allowing said emulsion to solidify, just before or during gelling of the emulsion, to form a network of two continuous phases, an aqueous polysaccharide phase and a flow-pore-forming organic phase, resulting in a material with two types of pores: small diameter diffusion pores and large diameter flow through pores.

2. The method according to claim 1, wherein the essentially water-immiscible phase is comprised of an oil in water detergent and an organic solvent.

3. The method according to claim 1, wherein the organic solvent is selected from the group consisting of cyclohexane, heptane and toluene.

4. The method according to any one of claims 1–3, wherein the polysaccharide comprises one or more polysaccharides selected from the group consisting of agarose, alginate, dextran and cellulose.

5. The method according to claim 4, wherein the polysaccharide is agarose and the solidification process is carried out by first mixing the emulsion with an essentially water-immiscible organic solvent, containing a water-in-oil-stabilizing detergent by stirring, and then lowering the temperature below the gelling temperature of agarose.

6. A porous polysaccharide material characterized by having two types of pores: small diameter diffusion pores and large diameter flow through pores.

7. The porous polysaccharide material according to claim 6, wherein the flow pores have a diameter greater than 0.5 micrometers.

8. The porous polysaccharide material according to claim 7, wherein the flow pores have a diameter smaller than 1 mm.

9. The porous polysaccharide material according to any one of claims 6 to 8, wherein the ratio between the flow pore diameter and the particle diameter is within the range 0.01–0.3.

10. The porous polysaccharide material according to claim 6, wherein the flow pores have a diameter greater than 5 micrometers.

11. The porous polysaccharide material according to claim 7, wherein the flow pores have a diameter smaller than 0.1 mm.

12. The porous polysaccharide material according to any one of claims 6 to 8, wherein the ratio between the flow pore diameter and the particle diameter is within the range of 0.05–0.2.

13. A method for producing porous materials of a polysaccharide, comprising the steps of:
   mixing a water-based solution of the polysaccharide with stirring, with an essentially water-immiscible organic phase to form an emulsion;
   allowing said emulsion to solidify, just before or during gelling of the emulsion, to form a network of two continuous phases, an aqueous polysaccharide phase and a flow-pore-forming organic phase; and
   removing said flow-pore-forming phase resulting in a material with two types of pores: small diameter diffusion pores having an average diameter of 20 to 500 angstroms and interconnected large diameter flow through pores having a diameter of 0.5–1000 micrometers, wherein the volume of said superpores in said porous material is in a range of about 15 to 50%.

14. The method of claim 13, wherein said flow-pore-forming phase is removed by dissolving said phase in a solvent in which said phase is soluble.

15. A porous polysaccharide material characterized by having two types of pores: small diameter diffusion pores having an average diameter of 20 to 500 angstroms and interconnected large diameter flow through pores having a diameter of 0.5–1000 micrometers, wherein the volume of said large diameter pores in said porous material is in a range of about 15 to 50%.

16. The porous polysaccharide material of claim 15, wherein the polysaccharide material is in the form of particles.

17. The porous polysaccharide material of claim 16, wherein the ratio between the flow through pore diameter and the particle diameter is within the range of 0.01–0.3.

18. The porous polysaccharide material of claim 16, wherein the ratio between the flow through pore diameter and the particle diameter is within the range of 0.05–0.2.

19. The porous polysaccharide material of claim 15, in the form of particles packed in a column.

20. The porous polysaccharide material of claim 15, in the form of particles, wherein the size of the flow through pores is in the range of 1/6 to 1/10 of the particle diameter.

21. The porous polysaccharide material of claim 15, in the form of a continuous bed.

22. The porous polysaccharide material of claim 15, in the form of a membrane.

23. A method for contacting liquids with a porous material which comprises:

passing a liquid to be treated through the porous polysaccharide material characterized by having two types of pores: small diameter diffusion pores having an average diameter of 20 to 500 angstroms and interconnected large diameter flow through pores having a diameter of 0.5–1000 micrometers, wherein the volume of said large diameter pores in said porous material is in a range of about 15 to 50%.

24. The method of claim 23, which involves chromatographic separation.

25. The method of claim 23, which involves membrane separation.

26. The method of claim 23, which involves solid phase chemistry.

27. A porous polysaccharide material produced by the method of claim 1.

28. A porous polysaccharide material produced by the method of claim 13.

29. A method for producing porous materials of a polysaccharide, comprising the steps of:

mixing a water-based solution of the polysaccharide with stirring, with an essentially water-immiscible organic phase to form an emulsion;

allowing said emulsion to solidify, just before or during gelling of the emulsion, to form a network of two continuous phases, an aqueous polysaccharide phase and a flow-pore-forming organic phase; and removing said flow-pore-forming phase resulting in a material with two types of pores: small diameter diffusion pores and large diameter flow through pores.

30. The porous polysaccharide material of claim 1, 6, 15, 16, 27 or 28 wherein said polysaccharide material is formed from agarose.

31. The method of claim 1, 13, 23 or 29, wherein said polysaccharide is agarose.

* * * * *